US012767642B2

(12) United States Patent
Gazzetto et al.

(10) Patent No.: US 12,767,642 B2
(45) Date of Patent: Oct. 20, 2026

(54) PROCESS FOR MANUFACTURING A MIXTURE COMPRISING A DIMERIC MACROCYCLE INTERMEDIATE OF A GADOLINIUM COMPLEX

(71) Applicant: BRACCO IMAGING S.P.A., Milan (IT)

(72) Inventors: Sonia Gazzetto, Cascinette d'Ivrea (IT); Valeria Boi, Strambino (IT); Andrea Banin, Collegno (IT); Andrea Barale, Bibiana (IT)

(73) Assignee: BRACCO IMAGING S.P.A., Milan (IT)

( * ) Notice: Subject to any disclaimer, the term of this patent is extended or adjusted under 35 U.S.C. 154(b) by 275 days.

(21) Appl. No.: 18/718,945

(22) PCT Filed: Dec. 13, 2022

(86) PCT No.: PCT/EP2022/085610

§ 371 (c)(1),
(2) Date: Jun. 12, 2024

(87) PCT Pub. No.: WO2023/110863

PCT Pub. Date: Jun. 22, 2023

(65) Prior Publication Data

US 2025/0051292 A1 Feb. 13, 2025

(30) Foreign Application Priority Data

Dec. 14, 2021 (EP) .................................... 21214326

(51) Int. Cl.
*C07D 257/00* (2006.01)
*C07F 11/00* (2006.01)

(52) U.S. Cl.
CPC .......... *C07D 257/00* (2013.01); *C07F 11/005* (2013.01)

(58) Field of Classification Search
None
See application file for complete search history.

(56) References Cited

U.S. PATENT DOCUMENTS 4,395,542 A * 7/1983 Sury .................... C07D 301/32 528/481
2023/0303592 A1 9/2023 Barale et al.
2024/0425527 A1 12/2024 Gazzetto et al.

FOREIGN PATENT DOCUMENTS

WO 2017098044 A1 6/2017
WO WO 2017/098044 * 6/2017 ........... C07D 257/02

OTHER PUBLICATIONS

Lucentini et al (Microchemical Journal 80:89-98, 2005) (Year: 2005).*
Shandong Qibo New Energy Co. (available online at https://www.qiboch.com/separation-method-of-epichlorohydrin/, Sep. 15, 2022) (Year: 2022).*
International Search Report and Written Opinion for PCT/EP2022/085610, mailed Mar. 13, 2023.
Moore, D.A., "Selective Trialkylation of Cyclen With tert-Butyl Bromoacetate [1,4,7,10-Tetraazacyclododecane-1,4,7-triacetic acid, Tri-tert-butyl Ester Hydrobromide]," Org. Synth., 85:10-14 (2008).

* cited by examiner

*Primary Examiner* — Craig D Ricci
(74) *Attorney, Agent, or Firm* — VIVICAR Law, PLLC

(57) ABSTRACT

The present invention relates to a process for the manufacturing of a mixture comprising the intermediate 1-[bis[2-hydroxy-3-[4,7,10-tris[2-(1,1-dimethylethoxy)-2-oxoethyl]-1,4,7,10-tetraazacyclododec-1-yl]propyl]amino]-1-deoxy-D-glucitol. Such intermediate is useful for the synthesis of the dimeric gadolinium complex [μ-[1-[bis[2-(hydroxy-κO)-3-[4,7,10-tris[(carboxy-κO)methyl]-1,4,7,10-tetraazacyclododec-1-yl-κ$N^1$,κ$N^4$,κ$N^7$,κ$N^{10}$]propyl]amino]-1-deoxy-D-glucitolate(6-)]]digadolinium complex, which can be employed as a contrast agent in the field of diagnostic imaging, and in particular of Magnetic Resonance Imaging (MRI).

22 Claims, No Drawings

PROCESS FOR MANUFACTURING A MIXTURE COMPRISING A DIMERIC MACROCYCLE INTERMEDIATE OF A GADOLINIUM COMPLEX

CROSS-REFERENCE TO RELATED APPLICATIONS

This application is the national stage application of corresponding international application number PCT/EP2022/085610, filed Dec. 13, 2022, which claims priority to and the benefit of European application no. 21214326.7, filed Dec. 14, 2021, which is hereby incorporated by reference in its entirety.

TECHNICAL FIELD

The present invention relates to the items characterized in the patent claims, namely to the chemical synthesis of a mixture comprising an intermediate dimeric macrocycle. The intermediate is employed in the synthesis of the dimeric gadolinium complex [μ-[1-[bis[2-(hydroxy-κO)-3-[4,7,10-tris[(carboxy-κO)methyl]-1,4,7,10-tetraazacyclododec-1-yl-κ$N^1$,κ$N^4$,κ$N^7$,κ$N^{10}$]propyl]amino]-1-deoxy-D-glucitolate(6-)]]digadolinium complex, which is useful in the field of diagnostic imaging and in particular of Magnetic Resonance Imaging (MRI).

BACKGROUND OF THE INVENTION

Magnetic Resonance Imaging (MRI) is a well-known diagnostic imaging technique that is used in clinical diagnostics for a growing number of indications. Gadolinium (Gd(III)) complexes are commonly used as contrast agents in MRI.

WO 2017/098044 discloses dimeric Gd(III) complexes useful as contrast agents in MRI, such as the dimeric Gd(III) complex [μ-[1-[bis[2-(hydroxy-κO)-3-[4,7,10-tris[(carboxy-κO)methyl]-1,4,7,10-tetraazacyclododec-1-yl-κ$N^1$, κ$N^4$,κ$N^7$,κ$N^{10}$]propyl]amino]-1-deoxy-D-glucitolate(6-)]] digadolinium complex (Compound 5 as herein referred)

Compound 5

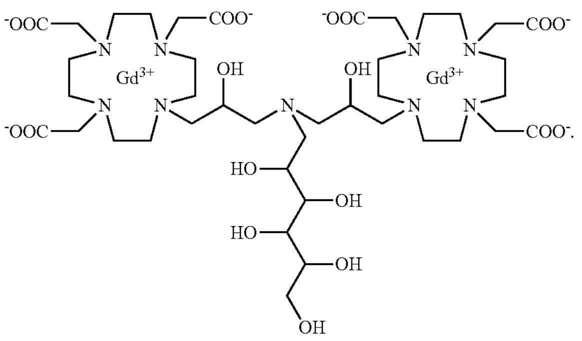

As disclosed in WO 2017/098044, Compound 5 displays a great relaxivity, and in particular a relaxivity that is more than 2-fold higher than the relaxivity displayed by Dotarem® and ProHance® (Non-Specific contrast agents currently in use in the diagnostic practice). Accordingly, Compound 5 is a promising contrast agent for in vivo MRI diagnostic imaging.

WO 2017/098044 further discloses the preparation of Compound 5 according to the following reaction scheme (Scheme 1):

Scheme 1

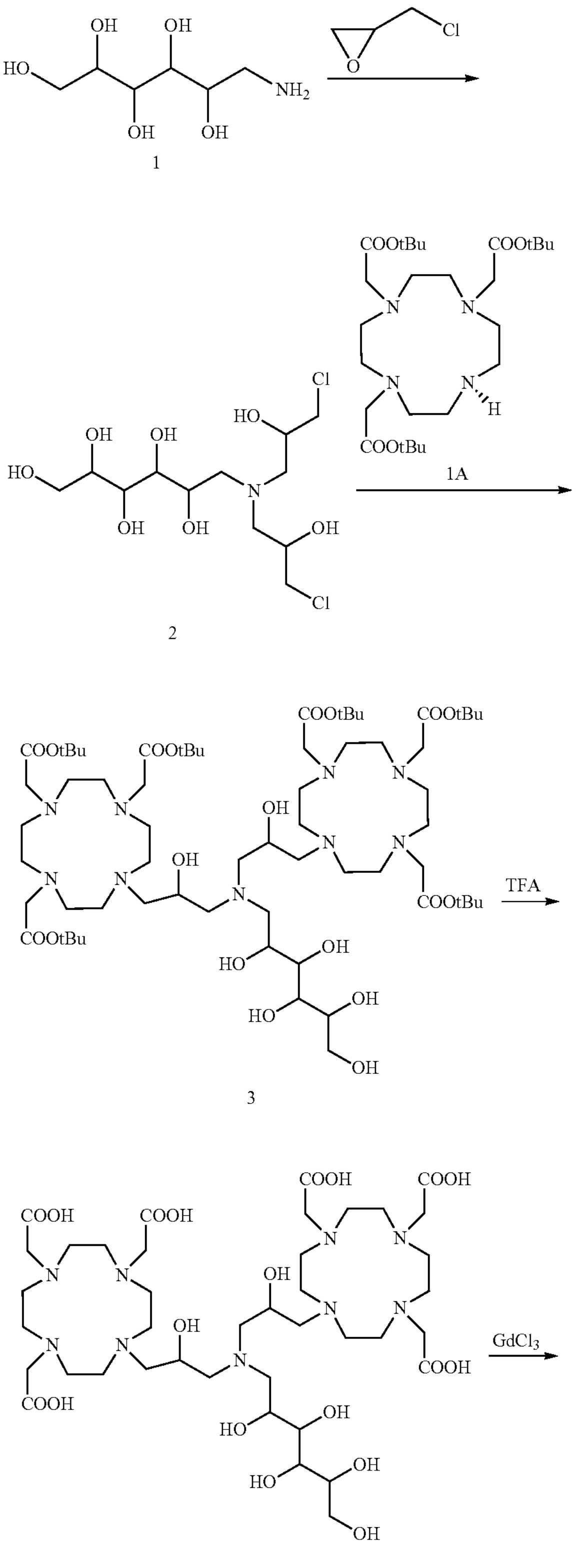

1

2

3

4

-continued

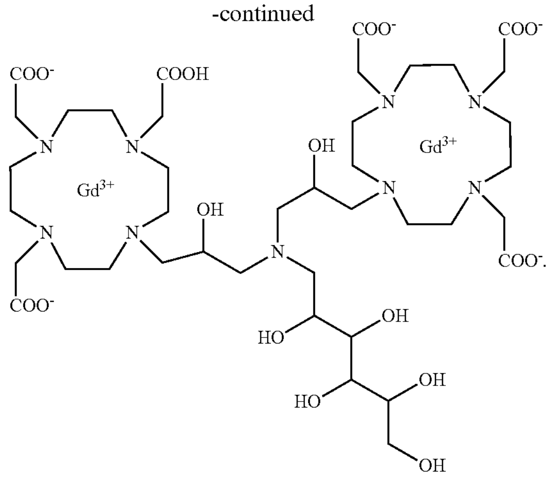

In particular, with reference to Scheme 1 above, WO 2017/098044 discloses the preparation of Compound 2 by adding a great excess of epichlorohydrin (52 mmol) to a solution of commercially available D-glucamine (10.5 mmol) in methanol, and subsequent reaction at 50° C. for 26 h. Compound 2 is then reacted with a stoichiometric amount of Compound 1A in acetonitrile in the presence of a base, $Et_3N$, at 70° C. for 72 h, to obtain the intermediate Compound 3 with a yield of 15%.

The process disclosed in WO 2017/098044 for the preparation of the intermediate Compound 3 (with reference to Scheme 1 above) has drawbacks, such as for instance long reaction times and low overall yields (in particular, in the step for obtaining Compound 3).

Moreover, the process disclosed in WO 2017/098044 provides for the isolation of all the intermediates, such as of intermediate Compounds 2 and 3, which is suboptimal for implementing the process on industrial scale In view of the above, there is the need to find an improved process for manufacturing Compound 5 and/or the intermediates thereof.

SUMMARY OF THE INVENTION

The present invention relates to a process for manufacturing a mixture comprising the intermediate Compound 3

Compound 3

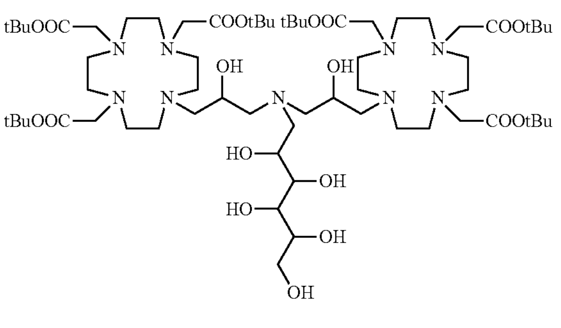

as set out in claim 1.

Compound 3 is a useful intermediate for the synthesis of Compound 5, as outlined in Scheme 1 above.

Notably, the process for manufacturing a mixture comprising Compound 3 allows avoiding isolating the intermediate Compound 2, making such process suitable and convenient for industrial scale.

Moreover, the process of the invention comprises the step of removing at least part of residual epichlorohydrin and derivatives thereof. As no isolation occurs during the process of the invention, the removal of epichlorohydrin and its derivatives (step b)) allows improving the efficiency of step c), i.e. of the coupling between Compound 1A and Compound 2. Indeed, it has been found that epichlorohydrin and its derivatives may react with Compound 1A during step c), thereby providing unwanted by-products, such as the by-products of the following formulae:

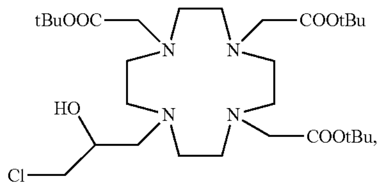

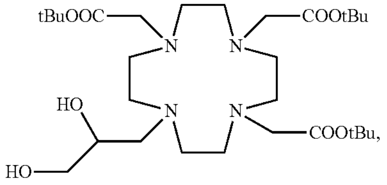

and thus reducing the amount of Compound 3 obtained. Accordingly, by removing part of epichlorohydrin and derivatives thereof via step b), the amount of epichlorohydrin and derivatives thereof is reduced, whereby less amount of epichlorohydrin and derivatives thereof can react with Compound 1A and the efficiency of the reaction of step c) is improved.

Furthermore, as epichlorohydrin is classified as probable or likely carcinogen in humans, the removal thereof is of paramount importance for a possible clinical application of the final product Compound 5, in particular when the process does not involve isolation of the intermediates, as set out in more details below.

The present invention further relates to a process for the manufacture of the dimeric complex Compound 5

Compound 5

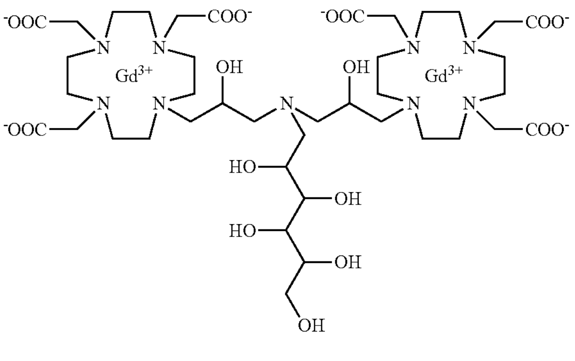

as set out in independent claim 14. This process for manufacturing Compound 5 is advantageously conducted without isolating the intermediates. As no isolation of the intermediates occurs, the removal of epichlorohydrin and derivatives thereof is even more so important to provide (i) an efficient process (i.e. reducing the unwanted reactions involving epichlorohydrin and derivatives thereof), and (ii)

a final product, i.e. Compound 5, comprising a reduced amount of harmful compounds (i.e. epichlorohydrin and derivatives thereof).

Specific embodiments of the processes above are set out in the dependent claims and in the next section.

DETAILED DESCRIPTION OF THE INVENTION

According to a first aspect, the present invention relates to a process for manufacturing a mixture comprising Compound 3 (i.e. of 1-[bis[2-hydroxy-3-[4,7,10-tris[2-(1,1-dimethylethoxy)-2-oxoethyl]-1,4,7,10-tetraazacyclododec-1-yl]propyl]amino]-1-deoxy-D-glucitol)

Compound 3

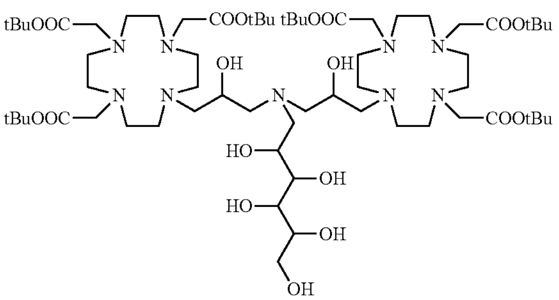

comprising the following steps:

a) reacting glucamine, preferably D-glucamine

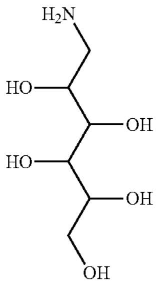

Glucamine with epichlorohydrin

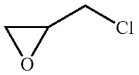

Epichlorohydrin within a solvent, preferably within an aqueous solution comprising at least a $C_1$-$C_3$ alcohol, such as methanol, thereby providing a first solution comprising Compound 2 (i.e. 1-[bis(3-chloro-2-hydroxypropyl)amino]-1-deoxy-D-glucitol)

Compound 2

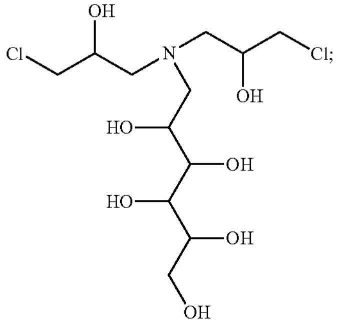

b) without isolating Compound 2 from the first solution, removing at least part of residual epichlorohydrin and derivatives thereof from the first solution comprising Compound 2, thereby providing a second solution comprising Compound 2;

c) without isolating Compound 2 from the second solution, admixing Compound 1A (i.e. 1,4,7,10-tetraazacyclododecane-1,4,7-triacetic acid 1,4,7-tris(1,1-dimethylethyl) ester), Compound 1A

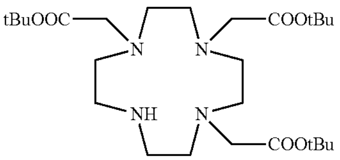

to the second solution comprising Compound 2, to react Compound 2 with Compound 1A, thereby providing the mixture comprising Compound 3.

As used herein, the term "mixture comprising Compound 3" refers to a mixture of Compound 3 with a solvent (in particular, the solvents disclosed in details below) that may further comprise other components, such as by-products (e.g. DO3A tBu·HCl) and unreacted reactants, in solution and/or suspension.

As used herein, the term "$C_1$-$C_3$ hydroxyalkyl" comprises within its meaning any linear or branched hydrocarbon chain comprising 1 to 3 carbon atoms and bearing one hydroxyl (—OH) group. Suitable examples are methanol, ethanol, propanol, and isopropanol thereof.

This process advantageously provides for manufacturing of a mixture comprising Compound 3 with high yields and low reaction times. Indeed, the reaction of step a) might be carried out for a time comprised in the range of 8 to 24 hours, preferably of 14 to 18 hours, more preferably for 16 hours, and/or at a temperature comprised in the range of 20 to 35° C., preferably of 23 to 28° C., and more preferably of 25° C., while the reaction of step c) might be carried out for a time of less than 72 hours, preferably less than 48 hours; the time can be more preferably comprised in the range of 14 to 24 hours, and even more preferably of 16 to 18 hours. The reaction of step c) is preferably carried out at a temperature comprised in the range of 55 to 75° C., preferably of 63 to 67° C. Not isolating Compound 2 allows to save further time and contributes making the process more suitable for industrial scale.

Furthermore, it has been found that the reaction of step a) can be carried out effectively by using a smaller amount of epichlorohydrin compared to the large excess of the same that is used in the prior art. This advantageously saves costs, as well as reduces the use of harmful compounds (as stated above, epichlorohydrin is classified as probable or likely carcinogen in humans) and of competing reactant (as stated above, epichlorohydrin might react with Compound 1A during step c), thus forming by-products) that have to be removed in the next step b). Indeed, according to a preferred embodiment, the reaction of step a) is carried out by reacting an amount of epichlorohydrin comprised in the range of 2.2 to 3.8 mol per mole of glucamine, more preferably of 2.5 to 3.5 mol per mole of glucamine, even more preferably of 2.9 to 3.1 mol per mole of glucamine, and most preferably an amount of epichlorohydrin of 3 mol per mole of glucamine.

It has also been found that the present process provides an improvement of the overall yield for obtaining Compound 3 compared to the process disclosed in WO 2017/098044.

Step a) provides for obtaining a solution comprising Compound 2 by reacting glucamine, preferably D-glucamine, with epichlorohydrin, both of which can be found commercially, e.g. according to the molar ratios provided above. In particular, according to a preferred embodiment, glucamine (preferably D-glucamine) is first dissolved in water, and such aqueous solution comprising glucamine is admixed (e.g. loaded over time, for example for a time comprised between 1 and 4 hours, preferably for 2 hours) to a mixture comprising epichlorohydrin diluted with a $C_1$-$C_3$ alcohol, preferably with methanol, preferably by maintaining the temperature at about room temperature (25° C.). Accordingly, the solvent of the reaction of step a) is preferably an aqueous solvent comprising a $C_1$-$C_3$ alcohol, preferably methanol.

Step b) allows removing residual epichlorohydrin (i.e. epichlorohydrin that has not reacted with glucamine during step a) and is thus present within the first solution comprising Compound 2), as well as derivatives thereof (i.e. derivatives of epichlorohydrin that might be generated during the reaction, namely 3-chloro-1,2-propandiol and 1,3-dichloro-2-propanol). Indeed, the second solution comprising Compound 2 obtained by step b) contains a lesser amount of epichlorohydrin and derivatives thereof compared to the first solution comprising Compound 2 obtained by step a) thanks to this purification step b), which has been found to effectively remove at least part of epichlorohydrin and derivatives thereof. In view of the above, step b) provides the advantage of removing harmful components from the solution, allowing in turn to improve the long-term safety of the final product (Compound 5) for its possible uses in clinical practice. Moreover, step b) advantageously removes harmful components without the need of isolating the intermediates (e.g. Compound 2). Step b) allows also improving the efficiency of the subsequent step c), as it allows reducing the amount of epichlorohydrin and derivatives thereof that compete with Compound 2 for the reaction with Compound 1A. This, and avoiding the isolation of Compound 2 during the process of the invention, further allows an increase in yields.

According to a preferred embodiment, removal of residual epichlorohydrin and the derivatives thereof, namely step b), is carried out according to the following steps:

- b1) removing a $C_1$-$C_3$ alcohol from the first solution comprising Compound 2, if present, preferably by distilling the $C_1$-$C_3$ alcohol from the first solution comprising Compound 2;
- b2) carrying out at least one liquid-liquid extraction, wherein the first liquid is the first solution comprising Compound 2, or the solution obtained by step b1) (if such step b1) is carried out), and the second liquid is any organic solvent immiscible with the first liquid, such as methyl ethyl ketone (MEK), methyl isobutyl ketone (MIBK), methyltetrahydrofuran (MeTHF), and methyl tert-butyl ether (MTBE). Preferably, the second liquid is MTBE.

The liquid-liquid extraction has been found to efficiently and effectively remove at least part of epichlorohydrin and the derivatives thereof from the first solution, thereby lowering the amount of harmful components. For example, and as better detailed in the Experimental Section, the first solution (i.e. before the liquid-liquid extraction) can contain an amount of epichlorohydrin, of 3-chloro-1,2-propandiol, and of 1,3-dichloro-2-propanol of up to 0.60%, 0.20% and 1.00% w/w vs. solution (respectively), while the second solution (i.e. after the liquid-liquid extraction) can contain an amount of the same compounds as low as 0.10%, 0.06%, and 0.05% w/w vs. solution (respectively). According to step b2), at least part of the residual epichlorohydrin and the derivatives thereof are removed from the solution by means of a liquid-liquid extraction. In particular, the first liquid (i.e. the first solution comprising Compound 2, or the solution obtained by step b1) (if such step b1) is carried out)) is preferably an aqueous solution, and the second liquid is preferably any solvent immiscible with aqueous solutions, such as the ones above mentioned. According to such embodiment, the residual epichlorohydrin and the derivatives thereof are extracted from the solution thanks to the organic solvent immiscible with the aqueous solutions (i.e. the second liquid of step b2)), such as MTBE, which can then be discarded.

During step b2), the first liquid is preferably an aqueous solution, and the solution obtained by (i.e. collected from) step b2) (the second solution) is also preferably an aqueous solution. Accordingly, the liquid-liquid extraction of step b2) is preferably carried out using as a first liquid an aqueous solution, and collecting the same after the extraction, and discarding the second liquid after the extraction.

Preferably, the liquid-liquid extraction of step b2) above is carried out more than one time, for example from two to four times, and preferably for three times.

According to a preferred embodiment, the amount of the second liquid immiscible with the first liquid is comprised within the range of 0.5 to 3 w/w, preferably of 1 to 2 w/w, more preferably of 1.2 to 1.8 w/w, and even more preferably of 1.5 w/w vs. the amount of glucamine of step a).

The solution comprising Compound 2 provided by step b) can be directly used for the next reactions steps without isolating the intermediate (Compound 2).

According to a preferred embodiment, the process comprises a solvent changing step after step b) and before step c), said solvent changing step comprising adding dimethyl sulfoxide (DMSO) to the second solution comprising Compound 2 and removing solvents (such as water) other than DMSO from said solution, whereby the second solution comprising Compound 2 after the present solvent changing step comprises DMSO as solvent. The amount of DMSO added according to this step can be comprised within the range of 2.0 to 4.0 w/w, preferably of 2.5 to 3.5 w/w, and more preferably is 3 w/w, vs. the amount of glucamine of step a). Preferably, after said solvent changing step, the residual water content (KF) is less than 15% w/w, and more preferably less than 6% w/w. The removal of solvents other than DMSO, e.g. the removal of water, from the second solution comprising Compound 2 added with DMSO, can be carried out by conventional means known to the skilled person, for example by distilling such solution under reduced pressure. According to the present solvent changing step, the second solution comprising Compound 2 has DMSO as solvent, and thus the subsequent reaction of step c) can be advantageously carried out in a reaction mixture comprising DMSO. This solvent changing step advantageously does not provide for isolating Compound 2. It has been found that this solvent changing step, and in particular the distillation of solvents (such as water) other than DMSO, further reduces the amount of epichlorohydrin and derivatives thereof, as disclosed in more details in the Experimental Section.

Step c) of the process of the invention provides for reacting Compound 2 as obtained by the upstream steps with preferably a molar excess of Compound 1A, thus obtaining a mixture comprising Compound 3. This reaction is preferably carried out by admixing the second solution comprising Compound 2, for example after the solvent changing step disclosed above, with a molar excess of Compound 1A, without isolating Compound 2 from the solution. Compound 1A can be prepared according to known methods, for example as disclosed in Moore D A, Org. Synth. 2008, 85, 10.

According to a preferred embodiment, the solvent of the reaction of step c) comprises DMSO and at least a $C_2$-$C_4$ alcohol, and preferably comprises DMSO and isopropanol. For example, step c) can be carried out by admixing the second solution, which preferably has DMSO as solvent (due to the solvent changing step, supra), with Compound 1A dissolved in a $C_2$-$C_4$ alcohol, preferably in isopropanol.

Step c) preferably employs a molar excess of Compound 1A, whereby Compound 1A conveniently acts as both a reagent and a base for the reaction of step c). Indeed, it has been found that a base is needed to neutralize hydrogen chloride that is formed during the present process. If not neutralized, hydrogen chloride can in turn react with the free amine of Compound 1A to generate Compound 1A hydrochloride (Compound 1A·HCl), which does not react with Compound 2 to form Compound 3. However, it has also been found that not all bases are as effective as Compound 1A to neutralize hydrogen chloride: for example, according to the process of the prior art WO 2017/098044, part of Compound 1A that should react with Compound 2 reacts instead with hydrogen chloride and is thus converted to Compound 1A·HCl, even if $Et_3N$ is used as a base. It has been surprisingly found that addition of a molar excess of Compound 1A overcomes this problem, thereby providing high yields for the present reaction step: indeed, by adding a molar excess of Compound 1A, Compound 1A is able to stoichiometrically react with Compound 2 to form Compound 3, while at the same time part of Compound 1A added in excess is able to effectively neutralize hydrogen chloride (forming Compound 1A·HCl).

Addition of a molar excess of Compound 1A also advantageously avoids the addition of a further component to the reaction mixture that acts as a base, such as $Et_3N$. This in turn avoids carrying out a specific purification step to remove such further component acting as a base.

Thus, according to a preferred embodiment, step c) is carried out by admixing more than 2.0 mol of Compound 1A per mole of Compound 2; preferably, up to 4.0 mol of Compound 1A per mole of Compound 2. For example, step c) is carried out by admixing 2.2 to 3.0 mol, preferably 2.4 to 2.8 mol, more preferably 2.5 mol of Compound 1A per mole of Compound 2.

As stated above, part of the excess of Compound 1A reacts with hydrogen chloride, thus generating Compound 1A·HCl. Compound 1A·HCl can be efficiently and effectively removed from the solution obtained from step c), i.e. from the mixture comprising Compound 3. Therefore, according to an embodiment, the process further comprises step d):

d) without isolating Compound 3 from the mixture, removing at least part of Compound 1A hydrochloride (Compound 1A·HCl) (e.g. formed during step c)) from the mixture comprising Compound 3, for example by precipitating Compound 1A·HCl.

Step d) is preferably carried out by:

d1) adding MTBE to the mixture comprising Compound 3 to precipitate at least part of Compound 1A·HCl; and d2) filtering the mixture obtained by step d1) to remove the precipitated Compound 1A·HCl.

The amount of MTBE added in step d1) is preferably comprised within the range of 2 to 10 w/w, more preferably of 3 to 4 w/w, and even more preferably of 3.6 w/w vs. the amount of glucamine of step a). The precipitation of step d1) can be preferably promoted by cooling the mixture to a temperature comprised between 5 and 15° C., more preferably between 8 and 10° C.

Step d), and in particular steps d1) and d2), advantageously allow to remove and possibly recover part of the excess of Compound 1A as Compound 1A·HCl in solid form (Compound 1A·HCl precipitated), thereby further improving the purity of the mixture comprising Compound 3 (and in turn of Compound 5 as obtained according to the manufacturing process disclosed below). Precipitated and filtered Compound 1A·HCl can be re-used again in step c) by converting it to Compound 1A, thus improving the cost-effectiveness of the process of the invention.

According to a preferred embodiment, the process of the invention further comprises the following steps:

d3) without isolating Compound 3 from the mixture, concentrating the mixture comprising Compound 3, or preferably the mixture obtained by step d) or d2); and d4) adding isopropanol and t-butyl bromoacetate to the mixture obtained by step d3), to obtain Compound 1B (DOTA 4tBu); preferably, Compound 1B is obtained by stirring at room temperature for an amount of time comprised in the range of 2 to 3 hours Compound 1B

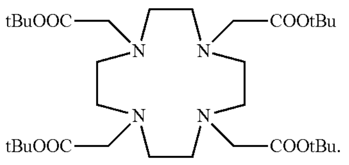

Step d4) allows obtaining Compound 1B (DOTA 4tBu). It has been found that a derivative of Compound 1B (i.e. Gd-DOTA, or the gadolinated complex of 2,2',2",2'"-(1,4,7,10-tetraazacyclododecane-1,4,7,10-tetrayl)tetraacetic acid) can be easily removed when the process for the manufacture of the dimeric complex Compound 5 (disclosed in more details below) is carried out: indeed, Compound 1B can be converted to its deprotected and gadolinated derivative (namely, Gd-DOTA) by simply carrying out the steps for manufacturing Compound 5 according to the invention (disclosed below), and Gd-DOTA can in turn be easily removed by means of chromatography, e.g. by chromatography using an ion exchange resin. In particular, once Compound 1A and/or Compound 1A·HCl (e.g. that does not precipitate during step d1)) are converted to DOTA 4tBu (Compound 1B) according to step d4), the latter can be first deprotected to obtain DOTA (2,2',2'',2'''-(1,4,7,10-tetraazacyclododecane-1,4,7,10-tetrayl)tetraacetic acid) by carrying out step f) (below), and finally complexed with gadolinium to obtain Gd-DOTA by carrying out step g) (below) according to the process for the manufacture of Compound 5 of the invention. Gd-DOTA can then be effectively removed by standard purification methods, such as chromatography via an ion exchange resin. This removal is very advantageous, as it has been found that Gd-DOTA can be removed more easily (e.g. by chromatography via an ion exchange resin) than the gadolinium deprotected derivative of Compound 1A, whereby it is preferable (in order to obtain a more effective purification) to deprotect, complex and then remove Compound 1B than the unreacted Compound 1A and/or the residual Compound 1A HCl that has not precipitated in step d1). Furthermore, Gd-DOTA removed as disclosed above can be advantageously collected (not discarded) and used in other process streams and/or for other purposes, as Gd-DOTA is a commercially marketed contrast agent.

Steps d1) to d4) advantageously allow to remove most of the excess of Compound 1A, thereby further improving the purity of the mixture comprising Compound 3 (and in turn of Compound 5 as obtained according to the manufacturing process disclosed below). Indeed, by carrying out steps d1) to d4), the HPLC analysis reveals that the percentage of the area under the curve (AUC %) of the peak relating to Compound 1A can be reduced from about 3.3% to about 0.2%.

Moreover, this method of purification is very advantageous also because it does not require isolating any intermediate (e.g. Compounds 3 or 4), which is beneficial for the manufacturing process in industrial scale.

Preferably, the solution obtained after step d4) is purified e.g. by chromatography using an adsorbent resin as stationary phase, to remove general impurities different from the ones specifically mentioned above (i.e. different from epichlorohydrin and derivatives thereof, and from Compound 1A HCl).

According to a preferred embodiment, the present invention relates to a process for the manufacture of the dimeric complex Compound 5

Compound 5

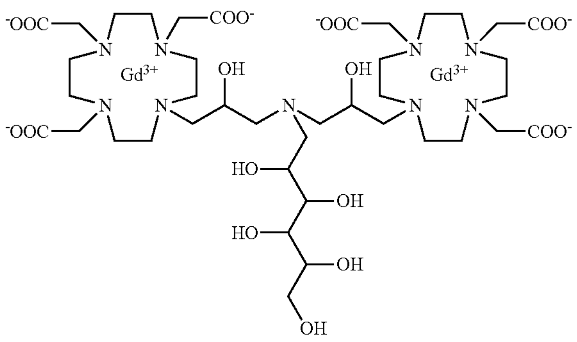

comprising the following steps:

e) manufacturing a mixture comprising Compound 3 according to any embodiments of the process for manufacturing a mixture comprising Compound 3 described above;

f) without isolating the compound from the mixture of step e), removing the tert-butyl protecting groups from Compound 3 to obtain a solution of a respective free ligand Compound 4

Compoud 4

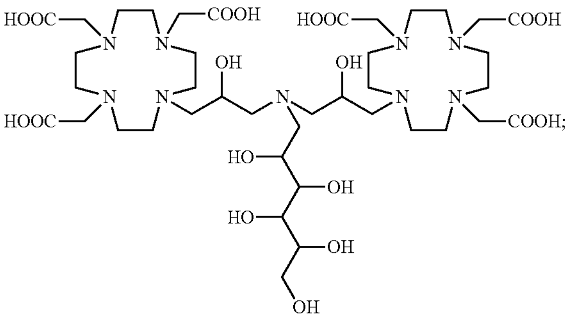

g) without isolating Compound 4, adding gadolinium metal ions to the solution of step f) to obtain a solution of the Compound 5; and h) collecting Compound 5, wherein the reaction solvent in all the steps following step e) is an aqueous solvent.

In the present description, the term "aqueous solvent" comprises within its meaning water and aqueous solutions, e.g. saline solutions, possibly including small amounts of organic solvents miscible with water, such as a volume percentage of 10% or lower of organic solvents miscible with water, preferably 8% or lower, and more preferably 5% or lower, acting as a solvent within a solution or mixture. Preferably the aqueous solvent is water.

Likewise, the expression "aqueous solution" includes in its meaning a solution comprising water. Suitable examples include a solution of one or more compounds, e.g. a reagent, an acid, a base or a reaction product in water.

This process provides for the manufacturing Compound 5 and encompasses all advantages of the process for manufacture of a mixture comprising Compound 3 disclosed above.

Moreover, the present process for manufacturing Compound 5 includes preparation steps carried out one-pot and without isolation of the resulting intermediates, which allow for both time saving and an improved overall yield and efficiency. Indeed, the prior art process requires the synthesis and isolation of each of the individual intermediates. Such isolation steps are particularly unsuitable for a large-scale production.

The prior art process is also unsuitable for working on larger scales, for example on industrial processes, because it encompasses the use of harsh materials that are difficult to handle, such TFA, TIPS and DCM, which might i.a. cause corrosion and thus wear out the synthesis apparatuses and/manufacture of Compound 5 or might not be safe for the health of the workers. On the contrary, the process for manufacturing Compound 5 avoids or strongly reduces the use of harsh reagents, such as trifluoroacetic acid (TFA), and nasty solvents, such as dichloromethane. Indeed, reaction solvent in all the steps following step e) is an aqueous solvent, and preferably does not comprise harsh materials such as TFA, TIPS and/or DCM. It has also been surprisingly found that using aqueous solvents in all steps after step e) does not provide a reduction of the overall yield of the process; on the contrary, the overall yield of the present process for manufacturing Compound 5 is improved compared to the process of the prior art.

In particular, using aqueous solvents as reaction solvent in all steps following the preparation of the coupling is very advantageous, particularly from the standpoint of costs, environmental impact, and ease of implementation in industrial scale. Indeed, the process disclosed in WO2017098044, uses solvent such as DCM and materials such as TFA and TIPS that beside being expensive are also difficult to handle, particularly when scaling the process on an industrial scale, and might also not be safe from a worker health point of view as well. As the process of the invention avoids or strongly reduces the use of organic solvents by using aqueous solvents in all the steps following the provision of Compound 3, the problem of the prior art process is solved by the present invention because the latter is suitable, and can be easily implemented, for working on larger scales, for example for working in industrial processes.

According to a preferred embodiment, before step f), the mixture comprising Compound 3 undergoes a solvent changing step, whereby the solvent of such mixture comprising Compound 3 after the solvent-changing step is an aqueous solution or water. In particular, if the mixture comprising Compound 3 has an organic solvent, the latter can be replaced with an aqueous one by methods known to the skilled person, e.g. by first diluting the mixture comprising Compound 3 with water, or with an aqueous solution, and then by removing the organic solvent to obtain an aqueous solution comprising Compound 3.

The step f) comprises the removal of the carboxyl protecting groups from Compound 3 to give an aqueous solution of the respective free ligand Compound 4. The deprotection by hydrolysis of tert-butyl protecting groups can be carried out in both acidic and basic conditions, by using reactants and conditions known to those skilled in the relevant art. In one embodiment, the deprotection is carried out by acidification of the aqueous solution of the protected ligand directly collected from the upstream steps, to achieve an acidic solution of Compound 4. The acidification is preferably carried out by addition of an acid, for instance selected from HCl, $H_2SO_4$, and $H_3PO_4$. In a preferred embodiment the deprotection is performed by using HCl. Then, the neutralization of the acidic solution, subsequent purification and partial concentration of the resulting mixture lead to collect an aqueous solution of Compound 4, that is used as such in the complexation step g), without isolation.

The step g) comprises the complexation of the ligand with gadolinium metal ions, to obtain the desired dimeric complex Compound 5. The complexation reaction can conveniently be carried out according to know procedures, for instance by stoichiometric addition of a suitable Gd(III) derivative, particularly an oxide such as $Gd_2O_3$ or a gadolinium salt, to the solution of the ligand. In one embodiment the complexation reaction is carried out by addition of $GdCl_3$ to the solution of the ligand directly collected from step f) of the process. The resulting mixture is adjusted to a pH value of from about 5 to about 7 and maintained under stirring to give an aqueous solution of the gadolinium complex Compound 5 that is then purified and concentrated to achieve solution of the desired dimeric complex Compound 5 having the desired purity.

The step h) comprises the final isolation of desired gadolinium complex Compound 5. This step can conveniently be carried out according to know procedures. In one embodiment the solution of the purified complex collected from step g) is spray-dried to give the desired product as a white solid satisfying the required purity specifications.

According to a more preferred embodiment, the process for manufacturing Compound 5 comprises the following steps:

e) providing a mixture comprising Compound 3 according to any embodiments of the process for manufacturing a mixture comprising Compound 3 as herein disclosed;
f) acidifying the solution from step e) to give an acidic aqueous solution of Compound 4, neutralizing the acidic solution and purifying the resulting neutral solution to give an aqueous solution comprising Compound 4, and, without isolation of the latter,
g) adding gadolinium metal ions to the solution of Compound 4 to obtain a solution of the corresponding complex Compound 5; and
h) isolating Compound 5.

Step f) comprises the deprotection of the protected ligand Compound 3 by removing carboxyl protecting groups leading to achieve an aqueous solution of the respective free ligand Compound 4. The reaction is preferably carried out by acidification of the aqueous solution of protected ligand of Compound 3 directly collected from step e) of the process.

In one embodiment step f) comprises:

i) addition of an acid to the aqueous solution of Compound 3 obtained after the solvent changing step disclosed above to achieve acidic solution of Compound 4;
ii) addition of a base to the acidic solution, to achieve a substantially neutralized solution of Compound 4;
iii) purification of the neutralized solution and subsequent optional concentration, to give an aqueous solution of Compound 4 that is suitable for use as such in the next complexation reaction, without requiring any isolation of the ligand.

In one embodiment, the solution of the protected compound of Compound 3 is acidified by addition of an acid, such as 34% aqueous HCl. The acidification is performed by using a large excess of HCl, e.g. from 30 to 100, preferably from 30 to 80, and, more preferably, of 40-50 times the molar amount of Compound 3.

The addition of the acid is carried out at a temperature of 20-35° C., preferably of 30-35° C. The resulting solution is then maintained under stirring at 30-40° C. for a time of from 10 to 36 h, preferably for 25-30 h, by following the deprotection of the ligand e.g. by chromatography.

The acidic solution is then cooled e.g. at 25° C., and then is neutralized by addition of a base, preferably NaOH, to achieve a raw solution with a final pH of from 6.5 to 7.5 which is then purified.

The purification steps preferably include: i) distillation of the neutralized solution, to remove the formed t-butanol, ii) desalination of the distillation residue, and iii) chromatographic purification of the desalinated solution.

In particular, in one embodiment, the solution resulting from the addition of a base is first distilled, preferably at a temperature of from 40 to 60° C. to remove formed t-butanol. The distillation residue is then desalinated, preferably by nanofiltration, and the collected solution is purified.

In one embodiment, the solution obtained by nanofiltration is first concentrated, for instance under vacuum at a temperature e.g. of 40 to 60° C., preferably of about 50° C., to a concentration preferably of 23-27% (w/w) and then is purified by elution on resins, more preferably on Amberlite XAD® 1600. The eluate is optionally treated with activated carbon, such as Carbopuron 4N®, and concentrated under vacuum at about 50° C. to achieve an aqueous solution of Compound 4 with final concentration preferably ranging from 8-25%, that is used as such in the next complexation reaction, without any isolation of the ligand.

Advantageously, the above procedure comprises using water as the sole or one of the main reaction solvent, thus avoiding or reducing the use of organic solvents, and in particular of harsh solvents, such as DCM, and of harsh reactant, such as TFA and TIPS, which are required in the process of above-mentioned prior art. These harsh materials are difficult to handle, and are thus unsuitable for use in large-scale productions. Moreover, this step leads to achieve the desired ligand in an aqueous solution ready for use in the complexation reaction, without requiring its isolation.

Step g) comprises the complexation of Compound 4 with gadolinium ions to achieve an aqueous solution of the desired chelated complex Compound 5.

More particularly, the step preferably comprises:

i) adding a gadolinium salt, such as $GdCl_3$ to the solution of Compound 4 to obtain a mixture comprising Compound 5;

ii) adding a base to give a mixture with a pH value of from about 5 to about 7;

iii) purifying the mixture, to give a solution of Compound 5; and iv) concentrating the collected solution.

The reaction is preferably carried out by addition of $GdCl_3$ directly to the solution of the ligand collected from the previous step of the process. The addition is preferably performed at a temperature of 25-45° C. The required amount of $GdCl_3$ leading to achieve the exhaustive complexation of the ligand is determined by titration of the ligand solution, for instance by using copper sulfate as titrating agent, according to know procedures.

In one embodiment, the ratio between ligand of Compound 4 and added $GdCl_3$ is from 1:1.98 to 1:2.02 (mol/mol); more preferably is of 1:2.00 to ensure the exhaustive consumption of the added lanthanide ion.

After the addition, the pH of the resulting mixture is adjusted to a value ranging from about 5 to about 7.5 by addition of a base, preferably NaOH.

For instance, in one embodiment $GdCl_3$ is added to the ligand solution e.g. at a temperature of 20-25° C. The resulting mixture is adjusted to a pH value of 7-7.5, such as about 7 by addition of NaOH, and then is maintained under stirring at 20-25° C. for about 25 h, thus achieving an exhaustive complexation of the ligand.

In one alternative embodiment, $GdCl_3$ and the necessary amount of NaOH for maintaining the pH at the desired neutral value can be added simultaneously, and the obtained mixture is then maintained under stirring for about 25 h, as above said.

In a preferred embodiment, the mixture resulting from the addition of $GdCl_3$ is adjusted to a pH value from about 5 to about 6, preferably from 5 to 5.6, more preferably of about 5.3, and then is maintained under stirring at about 40° C. for 1-4 h, e.g. about 2 h. The optional presence of residual free species such as free $Gd^{3+}$, ligand or partially complexed ligand is then assessed, e.g. by titration and/or HPLC methods, and compensated by addition of calculated amounts of ligand or $GdCl_3$ to give an aqueous solution of the dimeric complex of formula 5 which is then purified.

The purification is preferably carried out by chromatography, preferably on resins.

In one embodiment the purification comprises the elution of the mixture resulting from the complexation reaction on a polymeric resin, preferably an Amberlite XAD® 1600 resins.

In another embodiment, the purification comprises a first elution of the mixture resulting from the complexation reaction on a chelating resin, for instance selected from Hi Trap IMAC FF, Lewatit MonoPlus TP 260, Lewatit TP 208, IRC748I, DIAION CR11, SiliaMets AMPA and SiliaMets DOTA, and preferably from Diaion CR11 and Amberlite IRC748, allowing to minimize any optional free gadolinium content, and the additional purification of the collected eluate on a polymeric resin, such as a Amberlite XAD® 1600 resin.

According to a practical implementation, a mixture adjusted to an about neutral pH value is properly purified by elution on Amberlite XAD® 1600 resin.

The mixtures resulting from adjustment of the solution pH to lower values, such as 5-5.6, are otherwise preferably eluted first on a chelating resin such as the Amberlite IRC748 or the Diaion CR11 resin. The collected eluates are then preferably re-adjusted to a pH value of about 5.5-6 and concentrated, preferably under vacuum at 50° C. to obtain an aqueous solution of the dimeric complex with a concentration preferably of about 25% (w/w) that is then purified on Amberlite XAD® 1600 resin.

Collected fractions are then optionally treated with charcoal and filtered. The resulting filtered solution is then preferably concentrated, for instance by distillation under vacuum at 45-55° C. to give a solution of the dimeric complex 5 with a final concentration of about 25% (w/w).

According to a preferred embodiment, a purification step is carried out after step g) and before step h), said purification step comprising purifying the solution obtained by step g) by means of a ion exchange resin to remove Gd-DOTA (i.e. DOTA complexed with gadolinium) that has been formed in step g). As stated above, Gd-DOTA can be present within the solution obtained after complexation (step g) because Compound 1A and/or the residual part of Compound 1A·HCl can be converted to DOTA tBu (Compound 1B) according to step d4), which in turn can be deprotected in step f) to DOTA, which can then finally be complexed with gadolinium in step g) to Gd-DOTA. The so-obtained Gd-DOTA can be easily and effectively removed from the solution containing Compound 5 according to the present purification step.

Step h) comprises collecting the dimeric complex Compound 5, namely by removing the solvent from the aqueous solution obtained from step g). The complex can be collected from the aqueous solution obtained from step g) for instance by lyophilization or by spray-drying. In one preferred embodiment the desired dimeric complex is obtained as a white solid by spray-drying the solution directly obtained from step g) of the process.

The overall yield of the process, determined from the limiting reactant (glucamine), is of at least 35%, preferably of 40%, more preferably of about 45%.

Some of the compounds herein disclosed (e.g. Compounds 2 to 5) have one or more asymmetric carbon atoms, otherwise referred to as chiral carbon atoms, and thus give rise to stereoisomers (e.g. enantiomers and/or diastereomers). The present invention can thus be adapted to provide a process for manufacturing (a mixture of) any such possible stereoisomers of Compound 3, of Compound 4, and of Compound 5, as well as their racemic mixtures, their substantially pure resolved stereoisomers, all possible geometric isomers, and pharmaceutical acceptable salts thereof, starting for example from suitable chiral reactants and/or separating the stereoisomer(s) of interest via chromatography, possibly via chiral chromatography.

EXPERIMENTAL SECTION

Material and Methods

Reactants and/or solvents employed in the instant process, unless specified otherwise, are known and readily available.

If they are not commercially available per se, they may be prepared according to method in literature known to the skilled person.

Non-limiting examples of preferred embodiments of the process of the invention are reported in the present section. Such examples are aimed to illustrate the invention in greater detail without limiting its scope.

Example 1—Synthesis of a Solution of Compound 2 and Removal of Epichlorohydrin and Derivatives Thereof Scheme 2

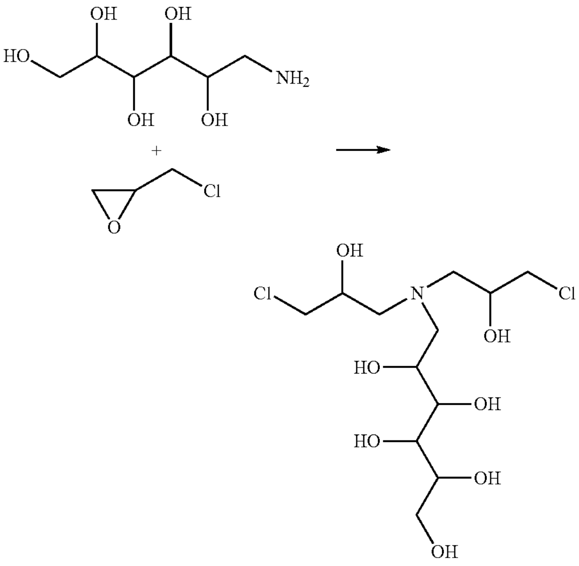

The reaction according to Scheme 2 is carried out as follows. D-glucamine (20.00 g, 0.11 mol) is loaded in a reactor (R1) and dissolved in water (40.00 g). The solution is transferred into a drum through a filter for eliminating the suspended particulate. The D-glucamine solution is loaded over 2 h into epichlorohydrin (30.64 g, 0.33 mol) previously diluted with methanol (40.00 g) in a second reactor (R2), maintaining the temperature around 25° C. At the end of the addition the first reactor (R1), the filter and the drum are rinsed with 10 g of water; this washing is collected into the second reactor (R2). The mixture is kept under stirring for 16 h. After reaction completion, methanol is distilled under slight vacuum (temperature: around 42° C.—vacuum: around 200 mbar). MTBE (30 g) is added to the aqueous solution and a liquid-liquid extraction is performed keeping under vigorous stirring the mixture for 20 minutes. After this time, the stirring is stopped in order to obtain the separation of two phases. The phases are separated and the extraction is repeated two more times (both with 30 g of fresh MTBE) following the same mode. To the aqueous phase obtained from the last separation, DMSO (60.0 g) is added. The mixture is concentrated distilling water under vacuum (temperature kept below 55° C., vacuum=40 mbar) until residual water content is less than 6% w/w. The obtained solution of Compound 2 is directly used for the next step (i.e. for Example 2).

Example 2—Synthesis of a Mixture Comprising Compound 3, and Removal of Residual Compound 1A·HCl Scheme 3

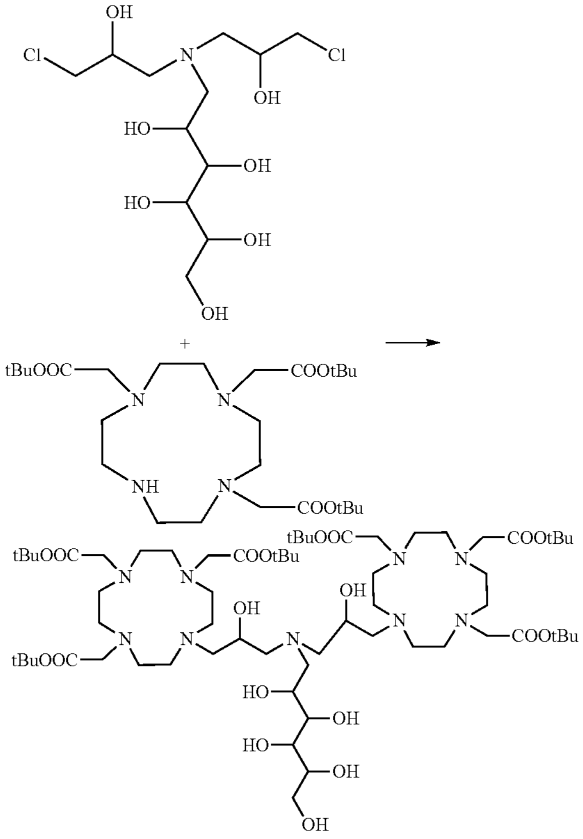

The reaction according to Scheme 3 is carried out as follows. To the solution of Compound 2 obtained by Example 1, Compound 1A (2.5 eq mol vs 1 mol of Compound 2) in isopropanol obtained as disclosed in Moore D A, Org. Synth. 2008, 85, 10 is added. The resulting mixture is kept under stirring for 17 h at 65° C. At the end of the reaction, the mixture is cooled down to 10° C. and MTBE (72.0 g) is added. Precipitate of Compound 1A·HCl, formed during the reaction, is removed by filtration. The cake is washed three times with MTBE (60 g each). The AUC % of the peak relating to Compound 1A is about 3.3%. The solution of Compound 3 is concentrated by distillation of isopropanol and MTBE at 50° C. under vacuum (100 mbar) and leaving a thick Compound 3 solution in DMSO. To this mixture, isopropanol (120 ml) and t-butyl bromoacetate are added to obtain Compound 1B (DOTA 4tBu); the mixture is maintained under stirring at room temperature for 2.5 h. The AUC % of the peak relating to Compound 1A is about 0.2%. After conversion, water (120 ml) and a 25% w/w ammonia solution (60 ml) are added to the mixture. The solution is loaded with a flow rate (0.5 BV/h) on a column packed with Amberlite XAD 1600N (overall amount of resin: 12 v/w of theoretical Compound 3), previously activated. The purification is performed with mixtures of isopropanol and water according the following elution gradient:

1. 4 bed volume of isopropanol 40: water 60 mixture
2. 4 bed volume of isopropanol 90: water 10 mixture The fractions to be collected are selected on basis evaluation of HPLC-UV analysis disclosed in detail below (Procedure 1). The fractions with high purity are loaded into a reactor and the mixture is concentrated by distilling under vacuum at maximum 50° C. Overall yield (Examples 1 and 2): 70%.

Example 3—Preparation of Compound 5

Deprotection of Compound 3 to Obtain Compound 4

34% hydrochloric acid aqueous solution (532.92 g; 4.97 mol) is added to the mixture obtained from Example 2 by maintaining the temperature at 30÷35° C. At the end of the addition, the mixture is heated to 37° C. and kept under stirring for 36 h. Then the solution is cooled to 25° C. and neutralized by addition of 30% sodium hydroxide aqueous solution, the t-butanol formed as by-product is removed by distillation and the mixture is desalinated by nanofiltration. The mixture is then partially concentrated at 50° C. under vacuum up to concentration of 24% w/w and purified by chromatography on Amberlite XAD® 1600 (1 L; eluent water). The fractions selected by evaluation on HPLC-UV are treated with charcoal and concentrated at 50° C. under vacuum to obtain a 10% w/w water solution of the desired ligand Compound 4 (0.0038 mol), which is quantified by potentiometric titration using a copper sulfate solution as titrating agent.

Complexation of Compound 4 to Obtain Compound 5, and Isolation of the Same

The solution of Compound 4 as obtained according to process above is heated to 37° C., then gadolinium chloride aqueous solution (40.76 g of gadolinium chloride in solution; 0.154 mol of gadolinium) is added maintaining the temperature in the range 37÷43° C. At the end of the addition, the pH is adjusted to 5.3 by addition of 10% sodium hydroxide aqueous solution. The mixture is maintained at 40° C. for 2 h with formation of the respective paramagnetic complex Compound 5. The presence of any free species is assessed e.g. by titration. The solution is then purified on Diaion CR11 chelating resin (0.16 L) reducing any free gadolinium content. After loading, the resin is washed with water, the pH adjusted to 5.5 and the solution concentrated under vacuum at 50° C. to obtain a 25% w/w water solution. This solution was loaded at pH 6 on Amberlite XAD® 1600 (3.3 L; eluent: gradient of water/MeCN). The fractions selected by evaluation on HPLC-FLD and UV are treated with charcoal and the resulting solution distilled at 50° C. under vacuum.

The final solution (25% w/w) is spray-dried to isolate the gadolinium complex as a white powder (70.8 corresponding to 64.4 g, as anhydrous product; titration assay: 99% w/w %, anhydrous base).

Overall yield from glucamine: 45%.

Example 4—Removal of Epichlorohydrin and Derivatives Thereof According to the Liquid-Liquid Extraction Step b)

Starting from different solutions of Compound 2 obtained according to step a) and comprising a different starting amount of epichlorohydrin and derivatives thereof, several trials of removal of epichlorohydrin and derivatives thereof according to the liquid-liquid extraction step b) have been carried out.

Table 1 reports the minimum and maximum amounts of epichlorohydrin and derivates thereof within different solutions (i) before the extraction (i.e. the starting amount), (ii) after the extraction, and (iii) after the solvent changing step (which comprises a distillation step—i.e. "After distillation" in Table 1). The amounts in Table 1 are expressed in % w/w vs. solution and were determined according to the method disclosed in Procedure 4 below.

TABLE 1

| Sample | Epichlorohydrin | 3-chloro-1,2-propandiol | 1,3-dichloro-2-propanol |
|---|---|---|---|
| Before extraction | 0.20-0.60 | 0.10-0.20 | 0.30-1.00 |
| After extraction | 0.10-0.15 | 0.06-0.09 | 0.05-0.08 |
| After distillation | 0.05-0.08 | 0.06-0.09 | 0.04-0.06 |

Table 1 clearly shows that the liquid-liquid extraction step b) allows removing at least part of epichlorohydrin and derivatives thereof. The removal of the same is further improved after distillation according to the solvent changing step.

Procedure 1

HPLC method: GEMINI DO3A

Column: Phenomenex Gemini 250 × 4.6 mm 5 um
Mobile phase: A = $CH_3COONH_4$ 0.2% + MeOH 2:1 B = $CH_3CN$ Gradient:

| t (min) | A | B | Flow (ml/min) |
|---|---|---|---|
| 0 | 60 | 40 | 0.7 |
| 5 | 60 | 40 | 0.7 |
| 30 | 10 | 90 | 0.7 |
| 35 | 10 | 90 | 0.7 |
| 36 | 60 | 40 | 0.7 |
| 45 | 60 | 40 | 0.7 |

Injection volume: 10 μl
Temperature: 40° C.
DAD detector: 212-240 nm
Diluent: $H_2O$/ACN 60/40

Procedure 2: HPLC Characterization and Determination of the Assay of the DO3A-Tri-Tert-Butyl Ester Chromatographic conditions

| | |
|---|---|
| HPLC system | Liquid chromatograph (e.g. Agilent 1100), equipped with solvent delivery system, autosampler, column thermostat, degasser and diode array detector or variable wavelength detector (or equivalent). |
| Stationary phase: | Zorbax Eclipse XDB-C8, 5 μm, 150 × 4.6 mm |
| Column temperature | 45° C. |
| Mobile phase: | A: 0.01M $K_2HPO_4$, 0.017M $H_3PO_4$<br>B: Acetonitrile |

| Elution: Gradient | Time (min) | % B |
|---|---|---|
| | 0 | 5 |
| | 30 | 80 |
| | 35 | 80 |
| | 38 | 5 |
| | 45 | 5 |

| | |
|---|---|
| Flow | 1 mL/min |
| Temperature | 45° C. |

-continued

| Chromatographic conditions | |
|---|---|
| Detection | UV, 210 nm, Bw = 8 nm; Reference 360 nm, Bw = 100 nm |
| Injection volume | 10 µL |
| Stop time | 35 min |
| Reference peak | DO3A 3tBu |
| Retention time | DO3A 3tBu ≅ 14-15 min. |

Procedure 3: HPLC Method for Monitoring the Formation and Purification of Compound 4

The monitoring of the formation and purification of the dimeric ligand Compound 4 were performed by reverse-phase HPLC with UV detection at 210 nm.

| Analytical conditions | | |
|---|---|---|
| HPLC system | Liquid chromatograph Agilent 1260 Infinity | |
| Stationary phase: | Synergi Polar-RP, 4 µm, 150 × 4.6 mm (Phenomenex, item 00F-4336-EO) | |
| Column temperature | 40° C. | |
| Mobile phase: | A: 10 mM $KH_2PO_4$<br>B: Methanol | |
| Elution: Gradient | Time (min) | % B |
| | 0 | 0 |
| | 5 | 0 |
| | 35 | 60 |
| | 40 | 60 |
| | 41 | 80 |
| | 46 | 80 |
| | 47 | 0 |
| | 60 | 0 |
| Flow | 0.8 mL/min | |
| Detection | UV/210 nm | |
| Injection volume | 10 µL | |
| Stop time | 60 min | |
| Compound 4 $R_t$ | 2.4 min | |

Procedure 4: GC Method for Determining the Amount of Epichlorohydrin and Derivatives Thereof

| | |
|---|---|
| Instrument: | GC system equipped with automated sample injector and a flame ionization detector, e.g. Agilent 6890 or equivalent<br>Column 1: Inlet Front Outlet Front Detector<br>Injector: Front<br>Channel: Channel 1<br>Pressure units: PSI<br>Auxiliary: Thermal |
| Capillary Column: | DB-624, 75 m, 530 µm i.d., 3 µm film thickness (Agilent J&W, P.N. 125-1374) |
| Liner: | GC Liner, Helix Open Ended Deactivated (Agilent Technologies, P.N. 5188-5396) |
| Oven: | set at 40° C. for 0 min; heat from 40° C. to 200° C., with a 5° C./min rate; hold at 200° C. for 0 min, heat from 200° C. at 250° C. with 100° C./min rate; hold time for 10 min<br>Equilibrium time: 1.00 min<br>Max Oven Temp: 260° C. |
| Front Inlet: | Automatic Liquid Sampler<br>Inlet type: Split/Splitless EPC<br>Injection temperature: 250° C.<br>Mode: split<br>Split flow: 20 mL/min<br>Split ratio: 5. |
| Front Injector: | Injection volume: 1 µL<br>Sol. A Pre-washes: 6<br>Sol. B Pre-washes: 0<br>Sample Washes: 2<br>Injector pumps: 3<br>Viscosity Delay: 3<br>Sol. A Post-washes: 0<br>Sol. B Post-washes: 10<br>Wash Solvent (Pre and Post): DMSO |
| Column 1: | Carrier gas: He<br>Outlet Pressure mode: Ambient<br>Column Pressure mode: Constant<br>Initial flow: 4.00 mL/min |
| Front detector: | FID, at 290° C.<br>Make up Gas: He<br>Flow Mode: Constant Makeup<br>Makeup Flow: 30 mL/min<br>Flame: enabled<br>Fuel flow (hydrogen): 40 mL/min<br>Oxidizer flow(air): 400 mL/min<br>Lit Offset: 0.5 pA |
| Channel 1: | Source: Front Det Output<br>Sampling rate: 20.0 |
| Run time: | 42.50 min (chromatograms to be evaluated until 30 min) |
| Reference peak: | Epichlorohydrin |

The invention claimed is:

1. A process for manufacturing a mixture comprising Compound 3

Compound 3

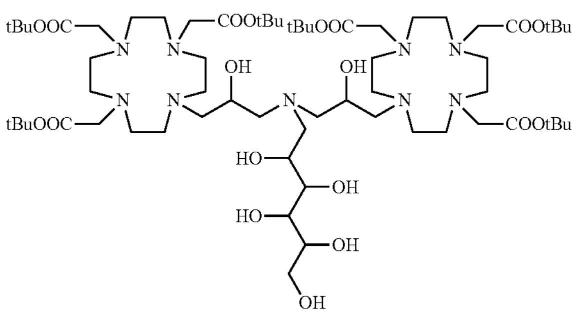

comprising the following steps:

a) reacting glucamine

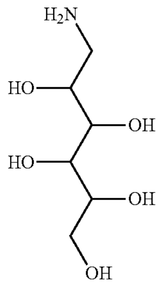

Glucamine with epichlorohydrin

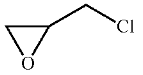

Epichlorohydrin within an aqueous solution comprising at least a $C_1$-$C_3$ alcohol, to provide a first solution comprising Compound 2

Compound 2

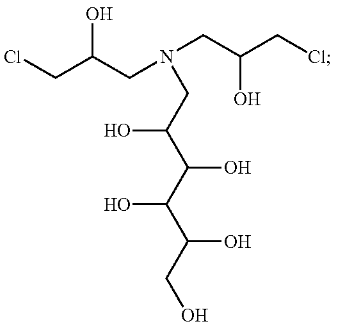

b) without isolating Compound 2 from the first solution, removing at least part of residual epichlorohydrin and derivatives thereof from the first solution comprising Compound 2 by
 b1) removing a $C_1$-$C_3$ alcohol from the first solution comprising Compound 2; and
 b2) carrying out at least one liquid-liquid extraction, wherein the first liquid is the solution obtained by step b1) and the second liquid is selected from the group consisting of methyl ethyl ketone (MEK), methyl isobutyl ketone (MIBK), methyltetrahydrofuran (MeTHF), and methyl tert-butyl ether (MTBE), thereby providing a second solution comprising Compound 2;

c) without isolating Compound 2 from the second solution, admixing Compound 1A

Compound 1A

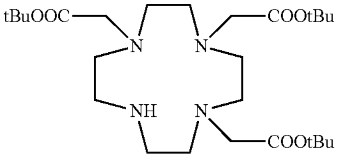

to the second solution comprising Compound 2, to react Compound 2 with Compound 1A, thereby providing the mixture comprising Compound 3.

2. The process according to claim 1, wherein said $C_1$-$C_3$ alcohol is methanol.

3. The process according to claim 1, wherein step a) is carried out by reacting an amount of epichlorohydrin comprised in the range of 2.2 to 3.8 mol per mole of glucamine.

4. The process according to claim 3, wherein step a) is carried out by reacting an amount of epichlorohydrin comprised in the range of 2.5 to 3.5 mol per mole of glucamine.

5. The process according to claim 4, wherein step a) is carried out by reacting an amount of epichlorohydrin of 3 mol per mole of glucamine.

6. The process according to claim 1, comprising a solvent changing step after step b) and before step c), said solvent changing step comprising adding dimethyl sulfoxide (DMSO) to the second solution comprising Compound 2, and removing solvents other than DMSO from the second solution comprising Compound 2 added with DMSO, whereby the second solution comprising Compound 2 comprises DMSO as solvent.

7. The process according to claim 6, wherein the second solution comprising Compound 2 and DMSO as solvent has a residual water content (KF) of less than 15% w/w.

8. The process according to claim 7, wherein the second solution comprising Compound 2 and DMSO as solvent has a residual water content (KF) of less than 6% w/w.

9. The process according to claim 1, wherein step c) is carried out by admixing Compound 1A in a molar excess with respect to Compound 2.

10. The process according to claim 9, wherein step c) is carried out by admixing more than 2.0 mol of Compound 1A per mole of Compound 2.

11. The process according to claim 10, wherein step c) is carried out by admixing up to 4.0 mol of Compound 1A per mole of Compound 2.

12. The process according to claim 11, wherein step c) is carried out by admixing 2.2 to 3.0 mol of Compound 1A per mole of Compound 2.

13. The process according to claim 1, wherein the reaction of step c) is carried out for a time of less than 48 hours.

14. The process according to claim 13, wherein the reaction of step c) is carried out for a time of 16 to 18 hours.

15. The process according to claim 1, wherein the reaction of step c) is carried out at a temperature comprised in the range of 55 to 75° C.

16. The process according to claim 15, wherein the reaction of step c) is carried out at a temperature comprised in the range of 63 to 67° C.

17. The process according to claim 1, wherein the reaction of step c) further comprises a solvent, wherein the solvent comprises DMSO and at least a $C_2$-$C_4$ alcohol.

18. The process according to claim 1, further comprising step d):
 d) without isolating Compound 3 from the mixture, removing at least part of Compound 1A hydrochloride (Compound 1A·HCl) from the mixture comprising Compound 3 by precipitating Compound 1A·HCl.

19. The process according to claim 18, wherein step d) is carried out by:
 d1) adding MTBE to the mixture comprising Compound 3 to precipitate at least part of Compound 1A·HCl; and
 d2) filtering the mixture obtained in step d1) to remove the precipitated Compound 1A·HCl.

20. The process according to claim 19, further comprising the following steps:
 d3) without isolating Compound 3 from the mixture, concentrating the mixture obtained by step d2); and
 d4) adding isopropanol and t-butyl bromoacetate to the mixture obtained by step d3) to obtain Compound 1B Compound 1B

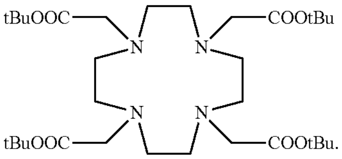

21. A process for the manufacture of the dimeric complex Compound 5

Compound 5

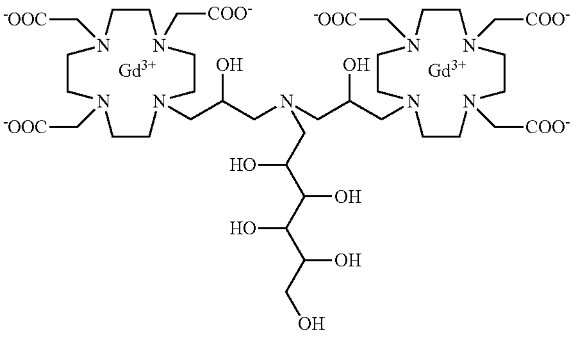

comprising the following steps:

e) manufacturing a mixture comprising Compound 3 according to claim 1;

f) without isolating the compound from the mixture of step e), removing the tert-butyl protecting groups from Compound 3 to obtain a solution of a respective free ligand Compound 4

Compoud 4

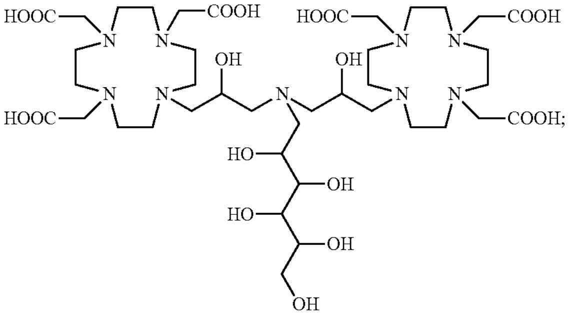

g) without isolating Compound 4, adding gadolinium metal ions to the solution of step f) to obtain a solution of the Compound 5; and h) collecting Compound 5, wherein the reaction solvent in all the steps following step e) is an aqueous solvent.

22. A process for the manufacture of the dimeric complex Compound 5 according to claim 21, wherein the process further comprises a purification step after step g) and before step h), said purification step comprising purifying the solution obtained by step g) by means of a ion exchange resin to remove the gadolinated complex of 2,2',2'',2''-(1,4,7,10-tetraazacyclododecane-1,4,7,10-tetrayl)tetraacetic acid (Gd-DOTA) that is formed during and/or after step g).

* * * * *